(12) United States Patent
Knoche

(10) Patent No.: US 7,030,340 B2
(45) Date of Patent: Apr. 18, 2006

(54) THERMOCYCLER

(75) Inventor: Jochem Knoche, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/859,420

(22) Filed: Jun. 2, 2004

(65) Prior Publication Data

US 2004/0265884 A1 Dec. 30, 2004

(30) Foreign Application Priority Data

Jun. 4, 2003 (DE) ................................. 103 25 300

(51) Int. Cl.
*C12M 1/34* (2006.01)
*C12M 3/00* (2006.01)
*C12Q 1/68* (2006.01)
*H05B 3/68* (2006.01)
*B01L 7/00* (2006.01)

(52) U.S. Cl. ....................... 219/385; 219/428; 219/430; 438/286.2; 422/64

(58) Field of Classification Search .................... None
See application file for complete search history.

(56) References Cited

U.S. PATENT DOCUMENTS

| | | | |
|---|---|---|---|
| 3,556,731 A | | 1/1971 | Martin |
| 4,902,624 A | * | 2/1990 | Columbus et al. ........ 435/285.1 |
| 5,167,926 A | * | 12/1992 | Kimura et al. ................ 422/67 |
| 5,525,300 A | | 6/1996 | Danssaert et al. |
| 5,632,956 A | * | 5/1997 | Ghaed et al. .................. 422/64 |
| 5,779,981 A | * | 7/1998 | Danssaert et al. ............ 422/99 |
| 6,183,693 B1 | * | 2/2001 | Bogen et al. .................. 422/64 |
| 6,210,958 B1 | | 4/2001 | Brust et al. |
| 6,303,322 B1 | | 10/2001 | Pantoliano et al. |
| 6,448,066 B1 | * | 9/2002 | Wheatcroft .............. 435/287.2 |
| 6,677,151 B1 | * | 1/2004 | Sandell .................... 435/287.2 |
| 6,875,602 B1 | * | 4/2005 | Gutierrez ................. 435/286.2 |
| 2002/0127660 A1 | | 9/2002 | Danssaert et al. |

FOREIGN PATENT DOCUMENTS

| | | |
|---|---|---|
| DE | 1 900 279 | 9/1969 |
| DE | 1900279 | 9/1969 |
| DE | 380 08 942 A1 | 9/1989 |
| DE | 196 46 114 A1 | 5/1998 |
| DE | 19646114 A1 | 5/1998 |
| EP | 0 318 255 A2 | 5/1989 |
| EP | 1 252 931 A1 | 4/2001 |
| WO | WO 95/11294 | 4/1995 |
| WO | WO 00/33962 | 6/2005 |

* cited by examiner

*Primary Examiner*—Joseph Pelham
(74) *Attorney, Agent, or Firm*—Brinks Hofer Gilson & Lione

(57) ABSTRACT

A thermocycler has, as heating devices, a plurality of heating blocks each with a respective coupling face, for heating at least one stationary specimen that during one temperature cycle has a plurality of temperature levels. The plurality of heating blocks is pivotably disposed, and the pivot axis is oriented perpendicularly to the coupling faces. The thermocycler is especially well suited for performing the polymerase chain reaction.

19 Claims, 3 Drawing Sheets

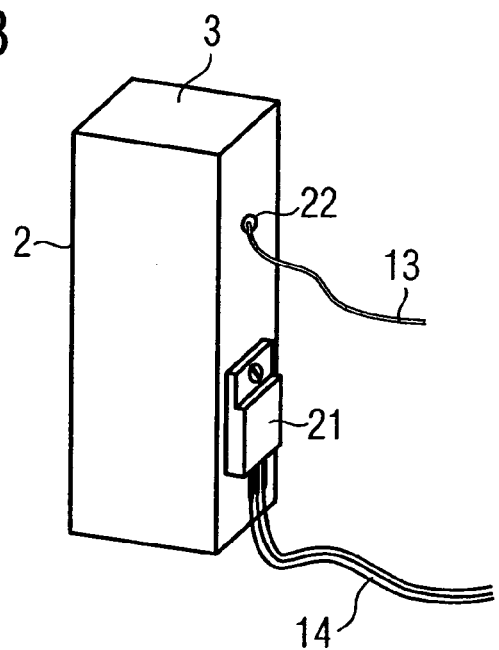
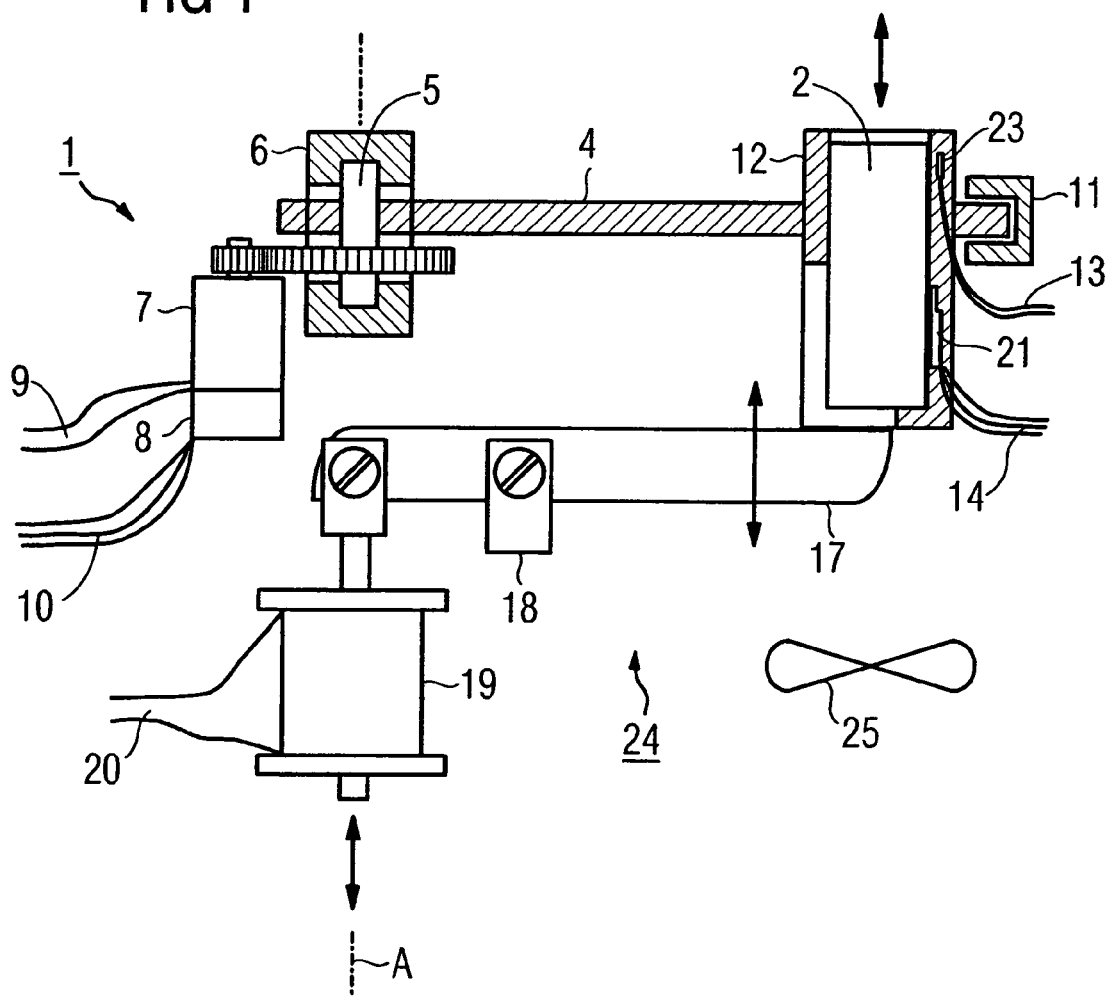

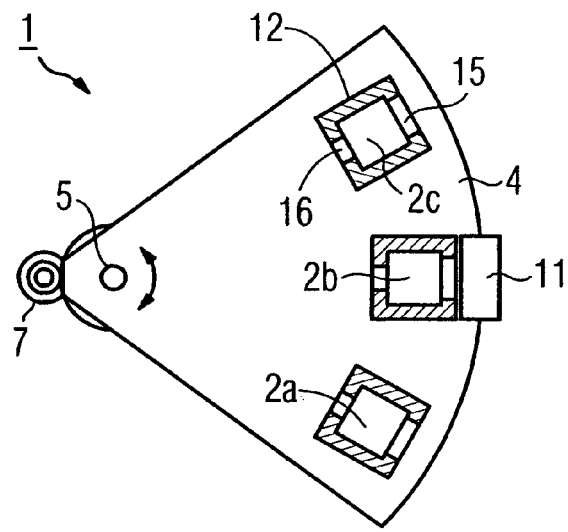
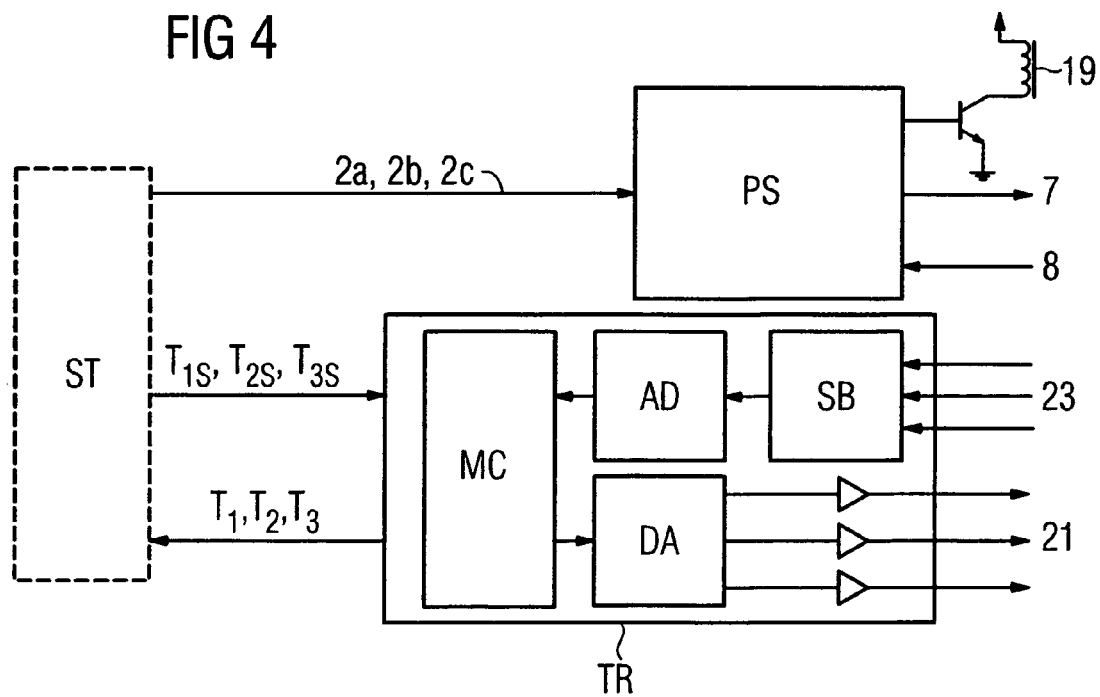

THERMOCYCLER

BACKGROUND

The invention relates to a Thermocycler or Thermal Cycler, in particular for a polymerase chain reaction, having at least two heating devices which predetermine a temperature level for heating a specimen. One such Thermocycler is known for instance from European Patent Disclosure EP 1 252 931 A1.

Polymerase chain reaction (PCR) is a method in molecular biology that makes it possible for any arbitrary base sequence of a DNA fragment of genetic information to be duplicated many times in a simple way. In order to attain amplification factors of over 100,000, for instance, by means of multiple duplications of a base sequence, a specimen to be processed passes through a defined temperature cycle multiple times, for instance 30 times. Within the defined temperature cycle, various fixed temperature levels are kept constant for a predetermined time, while transitions between the individual temperature levels should be as short as possible.

In an apparatus known from German Patent Disclosure DE 38 08 942 A1, the temperature control is performed by placing heated liquids in succession in an incubation chamber which contains incubation cells filled with specimens. Re-circulating the liquids, however, entails considerable expenditure of time. Alternative methods use air for heating up specimen holders, containers or vessels; in that case, the lesser thermal capacity of the air in comparison to a liquid is a disadvantage, as is a lower heat transfer rate at a surface of the specimen holders. Such a method is therefore contemplated primarily for very small specimen holders.

Another conventional method for heating up specimen holders employs Peltier elements. A use of this method, too, is limited by a size of the specimen holders, since as the Peltier elements increase in size, their thermal inertia also increases. Because of this size limitation, heating by means of Peltier elements is practically unusable in methods in which a specimen holder also serves to perform other processing and analysis steps, in addition to the PCR method.

From German Patent Disclosure DE 196 46 114, a Thermocycler is known in which, by means of a structurally complicated displacement and rotation system, heating blocks are meant to be put in an alternating manner into contact with the specimens to be heated.

OBJECT AND SUMMARY OF THE INVENTION

The present invention is defined by the appended claims. This description summarizes some aspects of the present embodiments and should not be used to limit the claims.

An object is to disclose a thermocycler, in particular for the PCR method, in a structurally simple embodiment, which enables a substantially fast transition between individual temperature levels of a specimen, the specimen being located in a container which in particular is suitable, in addition to performing the PCR method, for performing further processing and/or analysis steps as well.

One embodiment of the thermocycler has a plurality of heating devices for heating at least one stationary specimen that has a plurality of temperature levels during one temperature cycle, wherein, as the heating devices, a plurality of movable heating blocks, each with a coupling face for heating the specimen, are provided. The plurality of movable heating blocks is pivotably disposed, and a corresponding pivot axis may be oriented perpendicularly to the coupling faces.

As for the heating devices, the plurality of heating blocks can be thermally coupled to a stationary specimen. Due to the stationary positioning of the specimen during one temperature cycle, damage to specimen holders by possible handling steps during the passage through the temperature cycle is reliably avoided. In general, the thermocycler is especially suitable for cases in which a specimen chamber cannot be moved from place to place, or can be so moved only at great effort and expense. Heating up the specimen using solid bodies, namely a plurality of heating blocks having different temperature levels, furthermore assures very short transition times between the various temperature levels, especially compared to methods in which various heated liquids have to be recycled. The heating blocks are preferably constructed geometrically simply, in particular as parallelepipeds, and have a flat coupling face for heating the specimen. Alternatively, the coupling face can take a form of an indentation in the heating block, thus providing an especially large area of heat transfer to the specimen holder.

In a structurally simple embodiment, the heating blocks are disposed pivotably, in particular in a support plate in which the pivot axis is parallel to the surface perpendicular to the coupling face of the heating blocks that is intended for heating the specimen. Particularly in this embodiment, the heating blocks are preferably displaceable perpendicularly to the respective coupling face by means of a hoisting device. The hoisting device here, again in a structurally simple embodiment, preferably includes a deflection lever which serves to move and in particular displace the heating blocks and is operably actuated by an actuator element, such as a tension magnet.

The heating devices embodied as heating blocks typically have a temperature higher than the ambient temperature, in particular temperatures between 20° C. and 100° C. To minimize heat dissipation from the heating blocks, in a preferred refinement, the heating blocks are surrounded, outside the respective coupling face, by an insulating sleeve.

The thermocycler is operably suited for most various sizes of specimens that are to be heated, and a primary field of use may not be treating miniaturized specimens. The heating blocks are preferably constructed geometrically simply, in particular being parallelepiped or cylindrical, and have a coupling area of preferably at least 1 cm². Because of the high heat storage and heat transfer capacity of the heating blocks, they are especially well suited for substantial quick heating or cooling even relatively large specimens, for instance with a heat transfer area of about 18 mm×18 mm.

In a preferred refinement, whether or not the heating blocks have an insulating sleeve, a fan may be provided for cooling the heating blocks outside the coupling face. Using such a fan may help prevent thermal overloading of thermocycler components and the temperature level to be set during the temperature cycle is subsequently easily kept substantially constant.

The heating blocks can be heated by arbitrary heating elements, such as resistance heating elements. In an advantageous embodiment, a power transistor is used as the heating element. The power transistor, such as a bipolar silicon transistor, has a temperature-dependent conducting-state voltage of the base-to-emitter path, and as a result can be used simultaneously as a temperature sensor. Whether or not the heating element is used for temperature measurement, the heating block preferably has a separate temperature sensor, and as a result, redundant temperature measurement and thus improved process safety and reliability are optionally attained.

For controlled setting or regulation of the individual temperature levels within the temperature cycle and for spatially and chronologically exact positioning of the heating blocks, suitable regulating and control devices are preferably provided, and the heating and positioning operations are linked with a common system controller.

A thermal storage capacity of the heating blocks can be utilized in a targeted way to achieve substantially fast temperature transitions. For instance in a case of a specimen to be cooled down, the temperature of the heating block may initially be set lower than the temperature level to be attained in the specimen.

One advantage resides in particular in the fact that by means of interchangeable heating blocks, a stationary specimen undergoes a temperature cycle with fast temperature changes in a gentle way; the specimen holder is preferably intended both for performing the PCR method and for further processing and/or analysis steps.

Further advantages will become apparent from the dependent claims and the description of exemplary embodiments. Exemplary embodiments of the invention will be described below in conjunction with the drawings.

BRIEF DESCRIPTION OF THE DRAWINGS

FIG. 1 illustrates one embodiment of a schematic cross-sectional view of a thermocycler for a PCR method;

FIG. 2 is a schematic plan view of one embodiment of the thermocycler;

FIG. 3 shows an embodiment of a heating block of the thermocycler

FIG. 4 illustrates one embodiment of a block circuit diagram of a thermocycler controller.

Elements and parameters corresponding to one another are provided with the same reference numerals in all the drawings.

DETAILED DESCRIPTION

Figure 5:
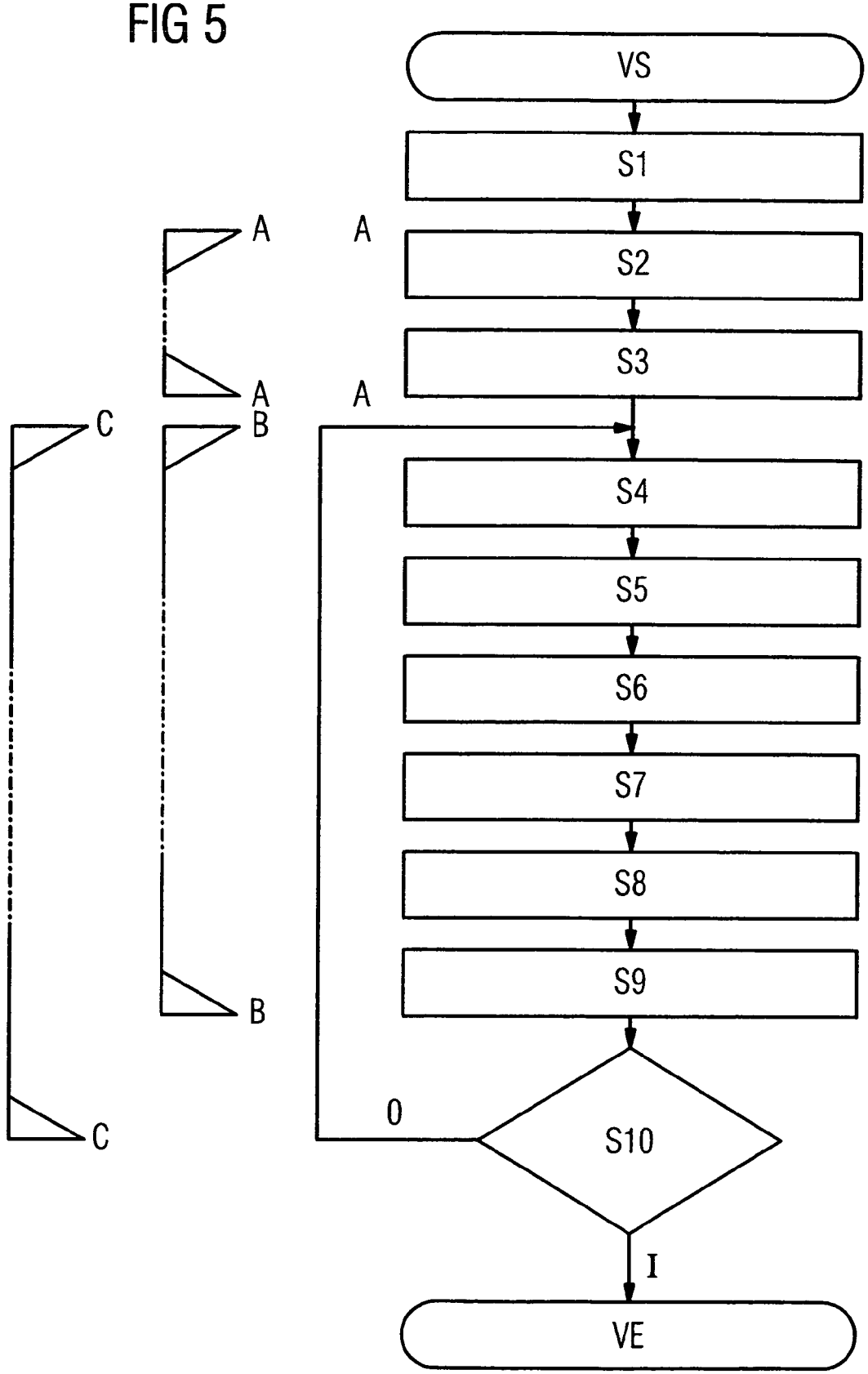
FIG. 5 illustrates a flow chart relaying a course of a polymerase chain reaction to be performed with the aid of the thermocycler in one embodiment.

A thermocycler 1 shown in simplified form in FIGS. 1 and 2 has three heating blocks 2; a first heating block 2a is intended for setting a temperature of 95° C., a second heating block 2b is intended for setting a temperature of 55° C., and a third heating block 2c is intended for setting a temperature of 72° C., in each case in a specimen holder, not shown, that is also known as a disposable cartridge. The specimen holder here is intended both for performing the polymerase chain reaction by means of the thermocycler and for further processing and analysis steps and is therefore larger than would be necessary for the polymerase chain reaction alone. A coupling face 3 of each heating block 2a, 2b, 2c has an area of 100 mm² or greater, as shown in FIG. 3.

The heating blocks 2a, 2b, 2c are supported and operably displaceable, as indicated in FIG. 1, by double-headed arrows, in a support plate 4 approximately in the shape of a segment of a circle; the support plate 4 is pivotable about a pivot axis A, disposed perpendicularly to the coupling faces 3, in such a manner that each of the heating blocks 2a, 2b, 2c can selectively contact the stationary specimen holder. In the region of the axis A, the support plate 4 is penetrated by a rotary peg 5 which is retained in a bearing block 6. A rotary drive mechanism 7 is embodied as a geared motor with an angle encoder and has position transducer/end switches 8, motor terminals 9, and position transducer terminals 10.

A guide element 11 of U-shaped cross section is disposed on a circularly curved circumferential portion of the support plate 4. The specimen to be heated is adjacent to the guide element 11. Each heating block 2a, 2b, 2c is displaceable perpendicularly to the respective coupling face 3 in a thermally insulating sleeve or sheath 12 serving as a holder. The respective sheaths 12 are secured rigidly in the support plate 4. Respective electrical terminals 13, 14 of the heating blocks 2a, 2b, 2c are extended flexibly through a slot 15 in the corresponding sheath 12. A further slot 16 in the sheath 12 enables a deflection lever 17, forming a part of a hoisting device 24, to engage the sheath 12 for displacing the heating block 2 (FIG. 1). The deflection lever 17 is supported in a bearing fork 18 and is operably actuated by a tension magnet 19 with electrical terminals 20. A shielding action of the sheath 12 may be reinforced by a fan 25, which delivers ambient air to regions outside the coupling face 3.

In the exemplary embodiment, the heating blocks 2a, 2b, 2c have identical shapes, but they may for instance have different masses.

As an embodiment of a heating device, one individual heating block 2 is shown in detail in FIG. 3. The parallelepiped heating block 2 is made of highly heat-conductive material, such as aluminum or copper or the like, and has a bipolar silicon transistor as its heating element 21. A temperature probe or sensor 23, such as a Pt100 probe or the like, is also located in a bore 22, closer to the coupling face 3. A thermal mass of the heating block 2 is markedly greater than a thermal mass of the specimen holder, including the specimen to be heated. By substantially good thermal coupling at the coupling face 3 and fast positioning of the heating block 2, short transition times between various temperature levels are attainable in the specimen.

A further increase in the cooling or heating speed in the specimen may be attainable by providing that the temperature of the heating block 2, before the cooling or heating operation, is lower or higher than the final temperature to be attained in the specimen. As such, the thermal storage capacity of the heating block 2 is also utilized for the temperature change in the specimen. This furthermore may facilitate a substantially exact regulation of the temperature of the specimen to be attained. For temperature regulation and/or monitoring, besides the temperature probe 23, the transistor 21 is also used, whose base-to-emitter path, which in electrical terms acts as a silicon diode, has a temperature-dependent conducting-state voltage. A drop in the conducting state voltage of approximately 2.2 mV/° C. is dictated invariably by material properties of the silicon, so that a temperature measurement is possible by measuring the conducting-state voltage. Thus the heating block 2 may have diverse (various) temperature sensors 21, 23.

FIG. 4 shows a simplified block circuit diagram of the electronic controller of the thermocycler 1. A system controller ST is linked here to both a position control device PS and a temperature regulating device TR. Information for selection of the heating block 2a, 2b, 2c is carried from the system controller ST onward to the position control device PS, which in accordance with this specification may interact with the tension magnet 19, the rotary drive mechanism 7, and the position transducer/end switches 8 and optionally other positioning and/or measuring devices.

The temperature regulating device TR may include a microcontroller MC, which receives set-point temperature values $T_{1S}$, $T_{2S}$, $T_{3S}$, specified by the system controller ST, for the temperature cycle to be passed through and reports current temperature values $T_1$, $T_2$, $T_3$ back to the system controller ST. Via an analog-to-digital converter AD and a digital-to-analog converter DA, respectively, the temperature probe 23 and the heating element 21 of each heating block 2a, 2b, 2c are connected to the microcontroller MC. Connected between the temperature probe 23 and the analog-to-digital converter AD is a signal processor SB, which although not shown is provided analogously for the heating element 21 as well, if this heating element is also used as a temperature sensor. The system controller ST and the microcontroller MC each may have an operably and respectively connected memory and corresponding software stored in these respective memories.

FIG. 5 is a flow chart illustrating a typical course of a polymerase chain reaction method known per se, performed with the aid of the thermocycler 1. Initially, the method start, which occurs at step VS, occurs at ambient temperature, such as 20° C. In a first method step S1, the cycle number $N_{cycle}$, typically from about 25 to 35, is specified. In a second method step S2, heating by means of the heating block 2a is done to the first set-point temperature $T_{1S}$, of 95° C. In method step S3, this temperature is maintained for about 4 minutes and 30 seconds. Note that the method steps S2 and S3 (block of consecutive method steps denoted by A—A in FIG. 5) serve the purpose of preparation for the next cycle.

In a fourth method step S4, the temperature $T_{1S}$ of 95° C. is maintained for about 30 seconds. This method step S4 is also called melting. A double-stranded DNA is separated here like a zipper into its two individual strands. In a next method step S5, cooling down is effected to the second set-point temperature $T_{2S}$ of 55° C., by means of the second heating block 2b. Before making contact with the specimen, the heating block 2b was heated to only about 50° C., for example, so that upon coupling to the specimen holder (cartridge), a heat excess is initially withdrawn from the specimen, and the temperature of the heating block is thus already raised to nearly 55° C. This rapid energy transfer from the specimen to a heating block 2b that has a suitable thermal mass simplifies the ensuing regulation to the set-point temperature $T_{2S}$ of 55° C. with the aid of the temperature regulating device TR. At method step S6, during which the specimen is kept at the temperature $T_{2S}$ for about 30 seconds is called annealing. During this annealing step, primers, which are short artificial DNA segments approximately 20 to 40 base pairs long, attach themselves to the individual DNA strands. Next, an enzyme DNA polymerase attaches itself to the attached primers.

In a seventh method step S7, the specimen is heated with the aid of the third heating block 2c to the third set-point temperature $T_{3S}$ of 72° C. and then, in method step S8, the specimen is kept at the temperature $T_{3S}$ for about 30 seconds. In a so-called elongation that occurs, the DNA polymerase travels along the single-stranded DNA, in the process creating the missing second strand.

In a passage through method steps S4 through S9 (block of consecutive method steps denoted by B—B) of the inner polymerase chain reaction loop (PCR loop), the DNA sequence is doubled. In a next method step S10, the question is asked whether the cycle number $N_{cycle}$ has already been reached. If not (symbol "0"), the temperature cycle is repeated, beginning with method step S4. The totality of all the temperature cycles S4 through S10 (block of consecutive method steps denoted by C—C) is also called an outer polymerase chain reaction loop. After method step S10, with the full cycle number $N_{cycle}$ (symbol "I"), a method end step VE is reached, in which the base sequence is present in a substantial quantity that may support successful chemical analysis.

The invention claimed is:

1. A thermocycler having a plurality of heating devices for heating at least one stationary specimen that during one temperature cycle has a plurality of temperature levels, the plurality of heating devices comprising;
   movable heating blocks, each of the plurality of heating blocks provided with a coupling face for heating the stationary specimen,
   wherein each of the plurality of movable heating blocks is pivotably disposed about a pivot axis, the pivot axis being oriented perpendicularly to the coupling faces of the plurality of heating blocks, and
   wherein the heating blocks are displaceable perpendicularly to a respective coupling face via a hoisting device, the hoisting device comprises a deflection lever.

2. The thermocycler of claim 1, wherein the heating blocks are retained in a pivotable support plate.

3. The thermocycler of claim 1, wherein the heating blocks are surrounded by an insulating sleeve outside the respective coupling faces.

4. The thermocycler of claim 1, wherein the coupling face of each of the plurality of heating blocks has an area of at least 100 mm$^2$.

5. The thermocycler of claim 1, further comprising a fan that cools the plurality of heating blocks outside of their respective coupling faces.

6. The thermocycler of claim 1, wherein each of the plurality of the heating blocks has a heating element.

7. The thermocycler of claim 6, wherein the heating element is a resistance heating element.

8. The thermocycler of claim 6, wherein the heating element is a power transistor.

9. The thermocycler of claim 1, wherein each of the plurality of heating blocks has a temperature sensor.

10. The thermocycler of claim 8, wherein the power transistor is provided as a temperature sensor.

11. The thermocycler of claim 8 further comprising a temperature regulating device.

12. The thermocycler of claim 1 further comprising a position control device.

13. The thermocycler of claim 1 further comprises a system controller operably cooperating with a temperature regulating device and a position control device.

14. The thermocycler of claim 1 further comprising a system controller linking a position control unit and temperature regulating device, such that a selection of a heating block is communicated to the position control device.

15. The thermocycler of claim 14, wherein the temperature regulating device includes a controller unit, which receives set-point temperature values specified by the system controller for a temperature cycle to be communicated to heating elements of each of the plurality heating blocks and reports temperature values collected by temperature sensors associated with each of the plurality heating blocks back to the system controller, the controller unit having a memory operably connected to the controller unit and a software stored in the memory.

16. The thermocycler of claim 15, wherein the temperature sensors and heating elements of each of the heating blocks are connected to the controller unit, the controller unit setting a temperature difference between the specimen to be heated by one of the plurality of heating blocks and the corresponding heating block before the specimen is put into contact with the coupling face of the corresponding heating block different than a temperature change in the specimen to be effected.

17. A thermocycler having a plurality of heating devices for heating at least one stationary specimen that during one temperature cycle has a plurality of temperature levels, the plurality of heating devices comprising:
movable heating blocks, each of the plurality of heating blocks provided with a coupling face for heating the stationary specimen,
wherein each of the plurality of movable heating blocks is pivotably disposed about a pivot axis, the pivot axis being oriented perpendicularly to the coupling faces of the plurality of heating blocks, and
wherein the heating blocks are displaceable perpendicularly to a respective coupling face via a hoisting device, the hoisting device comprises a tension magnet.

18. A method for heating a specimen in a thermocycler, having a plurality of heating blocks for heating at least one specimen that during one temperature cycle has a plurality of temperature levels, the method comprising:
moving the plurality of heating blocks, each of the plurality of heating blocks provided with a coupling face for heating the specimen; and
setting a temperature difference between the specimen to be heated by one of the plurality of heating blocks and the corresponding heating block before the specimen is put into contact with the coupling face of the corresponding heating block different than a temperature change in the specimen to be effected.

19. The method of claim 18, wherein setting the temperature comprises setting the temperature difference between the specimen to be heated by the one of the plurality of heating blocks and the corresponding heating block before the specimen is put into contact with the coupling face of the corresponding heating block higher than a temperature change in the specimen to be effected.

* * * * *